United States Patent [19]
Rex

[11] Patent Number: 5,542,411
[45] Date of Patent: Aug. 6, 1996

[54] MANUALLY OPERATED DISPENSER FOR DISPENSING A PREDETERMINED AMOUNT OF POWDERED SUBSTANCE

[75] Inventor: Jørn Rex, Roskilde, Denmark

[73] Assignee: Novo Nordisk A/S, Bagsvaerd, Denmark

[21] Appl. No.: 267,325

[22] Filed: Jun. 28, 1994

Related U.S. Application Data

[63] Continuation of Ser. No. 53,502, Apr. 27, 1993, abandoned, which is a continuation of Ser. No. 602,255, filed as PCT/DK90/00273, Oct. 24, 1990, abandoned.

[30] Foreign Application Priority Data

Nov. 1, 1989 [DK] Denmark ................... 5445/89

[51] Int. Cl.$^6$ .................... A61M 15/00; A61M 16/10
[52] U.S. Cl. .................. 128/203.15; 128/203.12; 128/203.21
[58] Field of Search ............ 128/200.14, 200.21, 128/200.22, 203.12, 203.15, 203.21, 203.24, 203.25

[56] References Cited

U.S. PATENT DOCUMENTS

| | | | |
|---|---|---|---|
| 2,587,215 | 2/1952 | Priestly | 128/203.15 |
| 3,921,637 | 11/1975 | Bennie et al. | 128/265 |
| 4,069,819 | 1/1978 | Valentini et al. | 128/203.15 |
| 4,114,615 | 9/1978 | Wetterlin | 128/173 |
| 4,116,195 | 9/1978 | James | 128/266 |
| 4,307,734 | 12/1981 | Blankenship | 128/203.15 |
| 4,811,731 | 3/1989 | Newell et al. | 128/203.15 |
| 5,033,463 | 7/1991 | Cocozza | 128/203.21 |

FOREIGN PATENT DOCUMENTS

| | | |
|---|---|---|
| 2102295 | 7/1981 | United Kingdom . |
| 81/01243 | 5/1981 | WIPO . |
| 9007351 | 7/1990 | WIPO ............... 128/200.22 |

Primary Examiner—Kimberly L. Asher
Attorney, Agent, or Firm—Steve T. Zelson Esq.; James J. Harrington Esq.

[57] ABSTRACT

A manually operated dispenser for dispensing a predetermined amount of powdered substance comprises a pressure cylinder (2) with an axially displaceable piston (3). A super-atmospheric pressure is generated by displacing the piston inwardly in the cylinder and is releaved through a chamber (41) in a magazine (40) comprising a number of chambers (41) containing powdered substance. The ends of the chambers (41) are covered by penetrable membranes (48), and the chambers (41) may be moved to successively being in alignment with a penetrator (30) and an outlet pipe (46). When the piston (3) is in its inner-most position the penetrator (30) and the inlet end of the out-let pipe (46) are forced through the respective membranes (48) at the ends of the chamber (41), and the subatmospheric pressure is releaved through the chamber (41) to dispense its content through the outlet pipe (46). The magazine (40) is annular and comprises a number of tubular chambers (41) placed equidistantly at some distance from and parallel with the axis of the magazine (40). At each full displacement of the piston (3) the magazine (40) is rotated to bring a new chamber (41) in alignment with the penetrator (30) and the outlet pipe (46).

14 Claims, 6 Drawing Sheets

MANUALLY OPERATED DISPENSER FOR DISPENSING A PREDETERMINED AMOUNT OF POWDERED SUBSTANCE

CROSS-REFERENCE TO RELATED APPLICATIONS

This application is a continuation of PCT/DK90/00273 filed Oct. 24, 1990, which is incorporated herein by reference.

This application is a continuation application of application Ser. No. 08/053,502, filed Apr. 27, 1993, now abandoned, which is a continuation application of application Ser. No. 07/603,255, filed Nov. 6, 1990, now abandoned.

This invention relates to a manually operated device (in the following referred to as a dispenser) for dispensing a predetermined amount of a powdered substance, said dispenser comprising a pressure vessel having means for generating a superatmospheric pressure within said vessel, a chamber containing a predetermined amount of the powdered substance and a passage serving to connect the pressure vessel with the chamber following the generation of a sufficiently high pressure within the pressure vessel to expel the powdered material from the chamber.

Devices of the above mentioned type are used, i.e., to dispense doses of powdered medicines and more particularly to introduce powdered medicines into the air passages and more particularly the nasal cavity of a patient.

U.S. patent specification No. 2,151,418 discloses a device of the above-mentioned type. This known device comprises a compressible bulb which is connected with a compartment containing a capsule containing a dosage unit of a powdered medicine, the capsule being adapted to open when a superatmospheric pressure produced by the compression of the bulb exceeds a given value.

The known device suffers from the drawback that a new capsule has to be inserted into the compartment before each dosing and that it is difficult to prepare capsules which open at a given pressure and which are completely emptied after being opened.

Another known device of the type in question is disclosed in the specification of Danish patent application No. 3942/74 (see U.S. Pat. No. 4,114,615). This known device comprises a compressible bellows, a capsule placed in a cavity, means for puncturing the capsule, and a mouthpiece for insertion in the patient's mouth. The mouthpiece communicates through the cavity with a valve mounted in the passage between the bellows and the capsule, said valve being designed to open when the patient produces a subatmospheric pressure in the mouthpiece by suction.

The dispensing of the powdered material contained in the capsule is effected only if the patient produces the vacuum necessary to open the valve and, therefore, the known device is unsuitable in cases where the patient is unable to produce such a vacuum e.g. due to traumas in the air passages or the oral cavity or due to the general weakness of the patient. The known device also suffers from the drawback that a new capsule has to be inserted before each dispensing.

The object of the invention is to provide a simple device of the type defined in the preamble, which device can be used for dispensing a series of exact dosages of a powdered substance without being dismantled and which only requires that the user contributes in generating the necessary superatmospheric pressure.

This object and other objects which will appear from the following description are achieved with the device of the invention, which device is characterized in that the pressure vessel comprises a pressure cylinder with an axially displaceable spring-loaded hollow piston and a one-way valve for the intake of air, valve means for connecting the interior of the cylinder to the inlet of said passage when the piston is displaced to its innermost position, the outlet end of said passage communicating with an inlet end of a chamber in a magazine comprising a number of chambers extending through said magazine and containing a powdered substance, the ends of said chambers being covered by penetratable membranes and said magazine being movable in such a manner that the inlet ends of the chambers therein can be moved successively into a position in which they are located in proximity to the outlet end of the passage.

SUMMARY OF THE INVENTION

According to the invention, the valve means may be provided by the portion of the hollow piston, which is in contact with the cylinder wall, comprising a hole which by axial displacement of the piston is brought into communication with a hole in the cylinder wall, which last hole is connected with the inlet end of the passage.

In the starting position the pressure within the pressure cylinder is atmospheric, but on axial displacement of the piston the pressure is gradually raised. The pressure rise will continue until the hollow piston reaches a position in which the valve means are activated to connect the interior of the cylinder to the inlet of the passage.

At this stage a pressure wave of a predetermined magnitude will generate in the passage and said pressure wave will propagate towards the chamber which is located in proximity of the outlet end of the passage.

When the device, including the strength of the membranes covering the ends of the chambers, is suitably dimensioned the pressure wave will propagate into the chamber which has its inlet end located in proximity of the outlet end of the passage and the pressure wave will cause the powdered material to be completely expelled from said chamber.

The spring-load on the piston will cause the piston to retract towards its starting position and at the same time air will flow into the cylinder through the one-way valve.

When the piston has returned to its starting position and when another filled chamber has been introduced into a position in which the inlet end thereof is located in proximity of the outlet end of the passage, the device is ready for dispensing a further dosage.

The specifications of UK patent application No. 2102295, DE published patent application No. 2654019 (see U.S. Pat. No. 3,921,637) and U.S. Pat. Nos. 2,672,144 and 3,425,414 also disclose devices for dispensing powdered substances.

However, contrary to the device of the invention the known devices are based on the use of a propellant contained in a pressure vessel.

The one-way valve is preferably located in the end wall of the piston and it preferably comprises an elastic flap covering a hole in the end wall. The elastic flap may be part of a rubber disc covering a substantial portion of the end wall. The spring-load on the piston is preferably established by a helical spring provided in the interior of the cylinder and one of the ends of the helical spring is preferably resting on the above mentioned rubber disc so as to keep the disc in place.

The piston preferably comprises a piston rod which is connected with an activator having means for restricting the withdrawal of the piston thus preventing the piston from being forced out of the cylinder by the helical spring.

The device of the invention preferably comprises means for mechanically penetrating the membrane provided at the inlet end of each chamber in the magazine when the chamber is in a position where the inlet end thereof is located in proximity of the outlet end of the passage. These penetrating means preferably comprise a penetrating means which is mounted so that it can be axially displaced in a passage provided in a housing surrounding the pressure cylinder.

In the embodiment wherein the valve means are provided by a hole in the piston wall being brought in alignment with a hole in the cylinder wall the penetrating means may be activated by a pressure rod. The pressure rod is preferably integral with said activator and its length is adapted so that shortly before the piston reaches the position in which the hole in the piston communicates with the hole in the cylinder wall the pressure rod exerts a pressure on the penetrating means and causes said penetrating means to be displaced towards the chamber containing the powdered substance over a distance sufficiently long to break the membrane covering the inlet end of the chamber.

Both membranes on the chambers are broken by first and second penetrating means.

In the embodiment wherein the valve means comprises a spring loaded valve the penetrating means may be integral with the valve to be activated with this valve by the piston when this piston is axially displaced to its innermost position.

In a particularly preferred embodiment of the device of the invention a portion of the passage extends through the interior of the penetrating means. The penetrating means preferably comprises elastic means for retracting the penetrating means towards its starting position when the pressure thereon is relieved and means for restricting the retraction.

The magazine is preferably located in a housing having a dispensing pipe having an inlet and an outlet end. The inlet end is preferably located in proximity of the downstream end of a chamber which is located in a position in which the upstream end (inlet end) is located in proximity to the outlet end of the passage. The dispensing pipe is preferably pointed at its inlet end so that a displacement of the magazine by the penetrating means causes the membrane covering the downstream end of the chamber to be broken.

When the device of the invention is to be used for nasal administration the downstream end of the dispensing pipe preferably has a shape so that it can be inserted into a nostril.

The magazine housing is preferably connected with the housing surrounding the pressure cylinder by means of a hinge.

The magazine preferably has an annular shape and it comprises a plurality of, e.g. 12, tubular chambers spaced equidistantly and located at the same distance from the axis of the magazine and with the axes of the tubular chambers being parallel. Such a magazine permits the chambers to be moved successively into a position in which they are placed coaxially with the passage and between said passage and the dispensing pipe.

Another preferred embodiment of the device of the invention further comprises means for automatically rotating the annular magazine after each dosing in order to bring a new chamber in position between the passage and the dispensing tube.

These rotation means preferably comprise a guide rod extending axially from the activator and having a free end located in a groove on the exterior surface of the annular magazine, said groove being composed of sections extending parallelly with the axis of rotation of the magazine alternating with sections forming an angle relative to said axis of rotation.

When the activator is depressed the free end of the guide rod is advanced through one of the first mentioned groove sections, and when the activator has reached the position in which powdered material is expelled from the chamber which is in the dispensing position the free end of the guide rod will have reached the end of said first groove section at which the groove section passes into a section forming an angle with the axis of rotation.

During the retraction of the activator to the starting position the free end of the guide rod will be withdrawn through the inclined groove section thus causing the annular magazine to rotate over an angle which is related to the inclination of the inclined groove section. When such a rotation has been effected a new cycle can be started.

BRIEF DESCRIPTION OF THE DRAWINGS

The invention will now be described in further detail with reference to the drawings in which.

DETAILED DESCRIPTION

The device shown in FIG. 1–4 comprises a cylinder housing 1 comprising a cylinder 2 surrounding a cup-shaped piston 3 which has a side wall 4 and an end wall 5. A hole 6 is provided in the side wall 4, and another hole 7 is provided in the end wall 5. The hole 7 in the end wall 5 is covered on the interior side of the piston 3 by a rubber flap 8 which is part of a rubber disc 9 covering a substantial part of the end wall 5 and being maintained in position by a helical spring 20 which at the opposite end of the cylinder 2 is centered by an annular projection 21.

Figure 1:
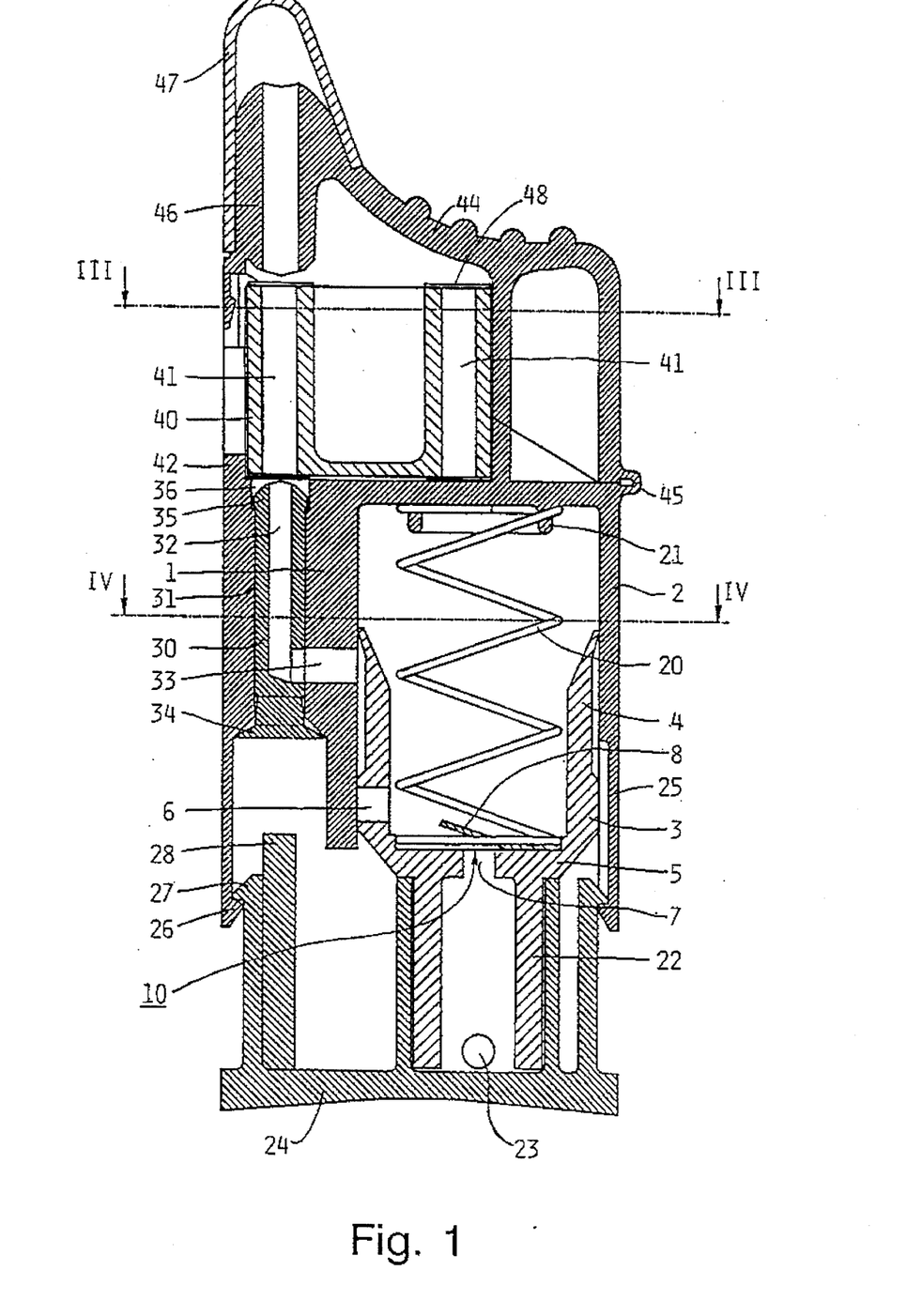
FIG. 1 shows a sectional side view of a preferred embodiment of the device according to the invention.

The piston 3 comprises a hollow piston rod 22 having an air inlet 23. An activator 24 is attached to the piston rod 22. The activator 24 is axially displaceable in a lower part 25 of the cylinder housing 1.

The lower part 25 of the cylinder housing 1 comprises at its free end an inwardly extending annular shoulder 26 which engages an outwardly extending annular flange 27 on the activator 24 when the latter is moved away from the cylinder 2. The activator 24 also comprises a pressure rod 28 which by activation of the activator 24 exerts a pressure on the end of a penetrating means 30 which is axially displaceable in a passage 31 in the cylinder housing 1.

The penetrating means 30 has an internal passage 32 which is connected with a hole 33 in the side wall of the cylinder 2. The end of the penetrating means 30 which faces the push rod 28 is fitted with an elastic annular flange 34 and at its opposite end the penetrating means 30 has an enlarged portion 35 which is mounted in a circular recess 36 in the cylinder housing 1. The elastic annular flange 34 and the thickened portion 35 of the penetrating means 30 ensure that the penetrating means 30 is axially movable over only a short distance and that it returns to its starting position when the pressure on the pressure rod 28 is relieved.

The thickened portion 35 of the penetrating means 30 is pointed.

The device further comprises an annular, rotatable magazine 40 which has twelve identical chambers 41 each filled with a powdered substance (not shown). The chambers 41 are closed at both ends by a breakable membrane 48. The magazine 40 is surrounded by an annular flange 42 in which there is provided a window 43 and which constitutes a lower part of a magazine housing. The annular flange 42 has an inclined end surface corresponding to a similar inclined end surface on an upper part 44 of the magazine housing which is connected with the cylinder housing 1 by means of a hinge 45, cf. FIGS. 1 and 2. The upper part 44 of the magazine housing comprises a dispensing pipe 46 which is pointed at the end facing the magazine 40. The outlet end of the pipe 46 is covered by a removable protection cap 47.

Figure 3:
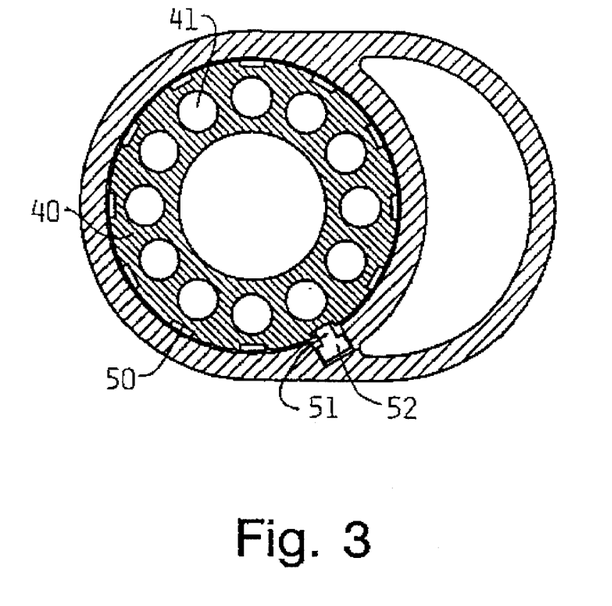
FIG. 3 shows a cross sectional view along the line III—III of the device shown in FIG. 1.
Figure 4:
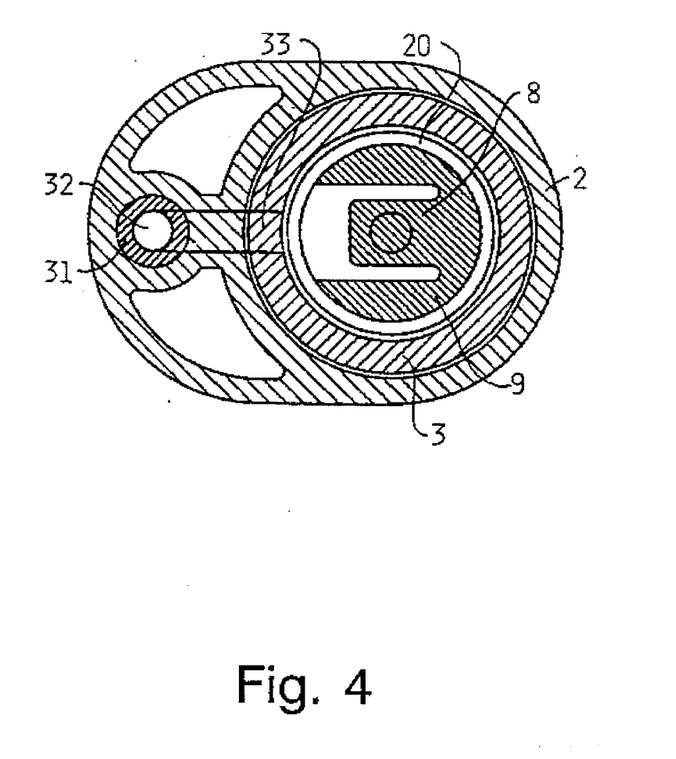
FIG. 4 shows a cross sectional view along the line IV—IV of the device shown in FIG. 1.

As will appear from FIG. 3 the exterior surface of the magazine 40 has a groove 50 for guiding a pin 51 provided at the free end of a guide rod 52 (see FIG. 5) extending from the activator 24 and being mounted so that it can be axially displaced in a passage (cf. FIG. 3) in the cylinder housing 1. The groove 50 comprises twelve axially extending sections 53 alternating with twelve sections 54 extending at an angle relative to the sections 53 and connecting the ends thereof except that the last inclined section 54 passes into a thirteenth axially extending section of the groove which leads to the lower terminal surface of the magazine.

Figure 5:
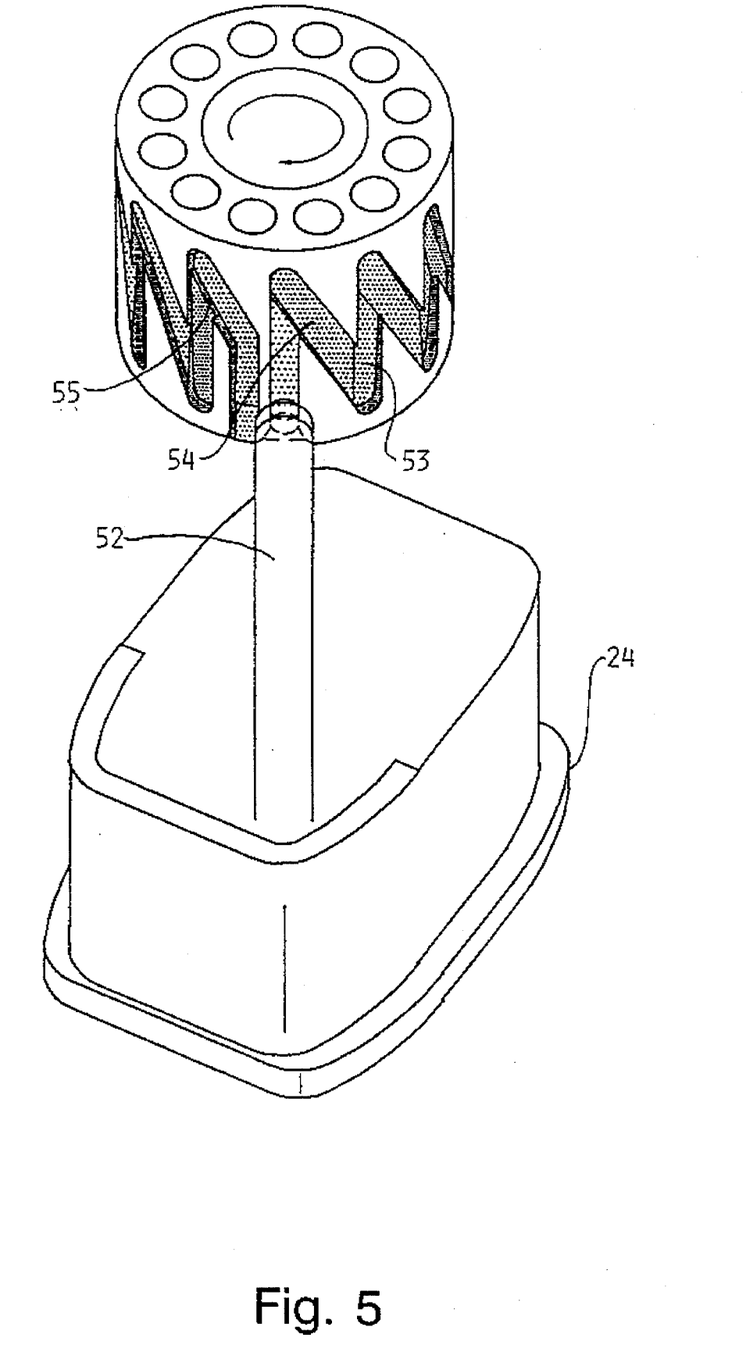
FIG. 5 is a schematic illustration of the mechanism for automatically rotating the magazine shown in FIG. 1–3.

The depth of the groove sections 53 and 54 varies in the zones at which an axial section 53 passes into an inclined section 54 thus providing surfaces 55 which ensure that the magazine can rotate in one direction only relative to the pin 51, cf. the arrow shown in FIG. 5.

The device illustrated operates as follows:

Before using the device the protective cap 47 is removed, and the outlet of the dispensing pipe 46 is placed in one of the nostrils of a patient. Subsequently, the activator 24 is depressed.

Such depression causes the one-way valve 10 comprising flap 8 to be pressed against the end wall 5 of the piston 3 so as to prevent air from escaping through the hole 7. By further depressing the activator 24 the pressure within the cylinder 2 is increased. The pressure increase continues until the holes 6 and 33 communicate. Shortly before this happens the pressure rod 28 will have pressed the penetrating means 30 against the magazine 40 and have displaced said magazine 40 towards the pointed end of the dispensing pipe 46 so as to break both of the membranes 48 covering the ends of the chamber 41 which is located in the dispensing position.

In this position there will be an open connection between the passage 32, the chamber 41, and the dispensing pipe 46 thus enabling the powdered substance to be expelled suddenly and completely from the chamber 41 when the holes 6 and 33 are brought into communication, and the pressure generated in the cylinder 2 is suddenly relieved.

The powdered substance expelled will pass from the chamber 41 to the dispensing pipe 46 and into the nasal cavity of the user.

On depressing the activator 24 the pin 51 travels through an axially extending groove section 53 and passes into the transition zone between the axially extending groove section 53 and the inclined groove section 54.

When the pressure on the activator is eased the helical spring 20 will return the piston and the activator to the starting position, and air will flow into the cylinder 2 through the hole 7 in the end wall 5 of the piston.

At the same time the pressure on the penetrating means 30 is relieved thus enabling the elastic annular flange 34 to bring the penetrating means 30 back to its starting position. During the retraction of the activator 24 the pin 51 will move through an inclined groove section 54 because the inclined surface 55 will prevent it from moving back into the axially extending groove section 53. Consequently, the magazine will be rotated over 30° so as to bring a new chamber 41 into dispensing position. The return of the activator 24 will stop when the annular flange 27 engages the shoulder 26.

The device is then ready for dispensing a new dosage.

Figure 2:
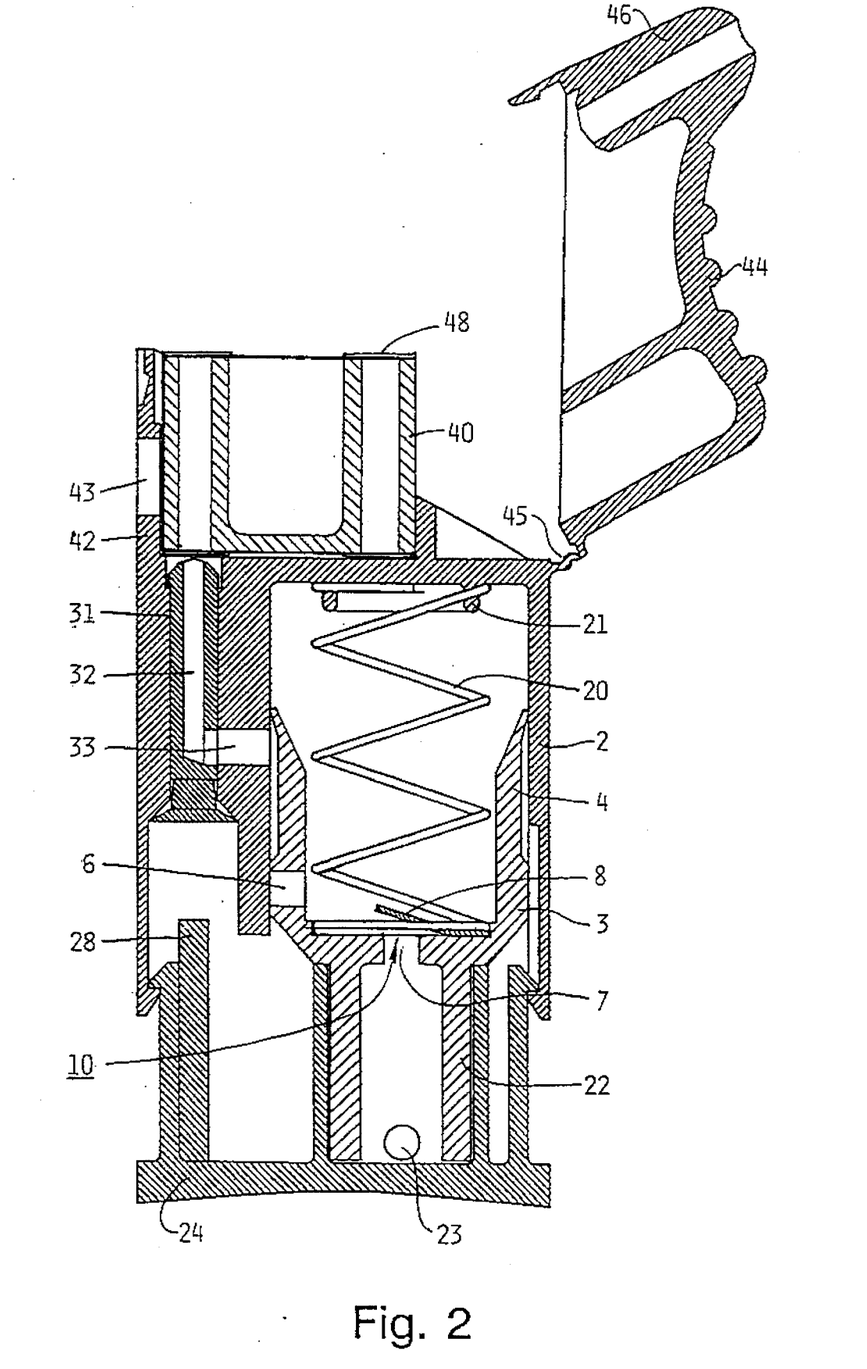
FIG. 2 shows a sectional side view corresponding to that of FIG. 1 but with the magazine housing opened and the protecting cap removed.

When all chambers have been emptied the magazine housing is opened as shown in FIG. 2, and a new filled magazine 40 is inserted.

When numbers readable through the windows 43 are provided on the external surface of the magazine 40 the user is able to determine the number of doses used or left without opening the magazine housing.

Figure 6:
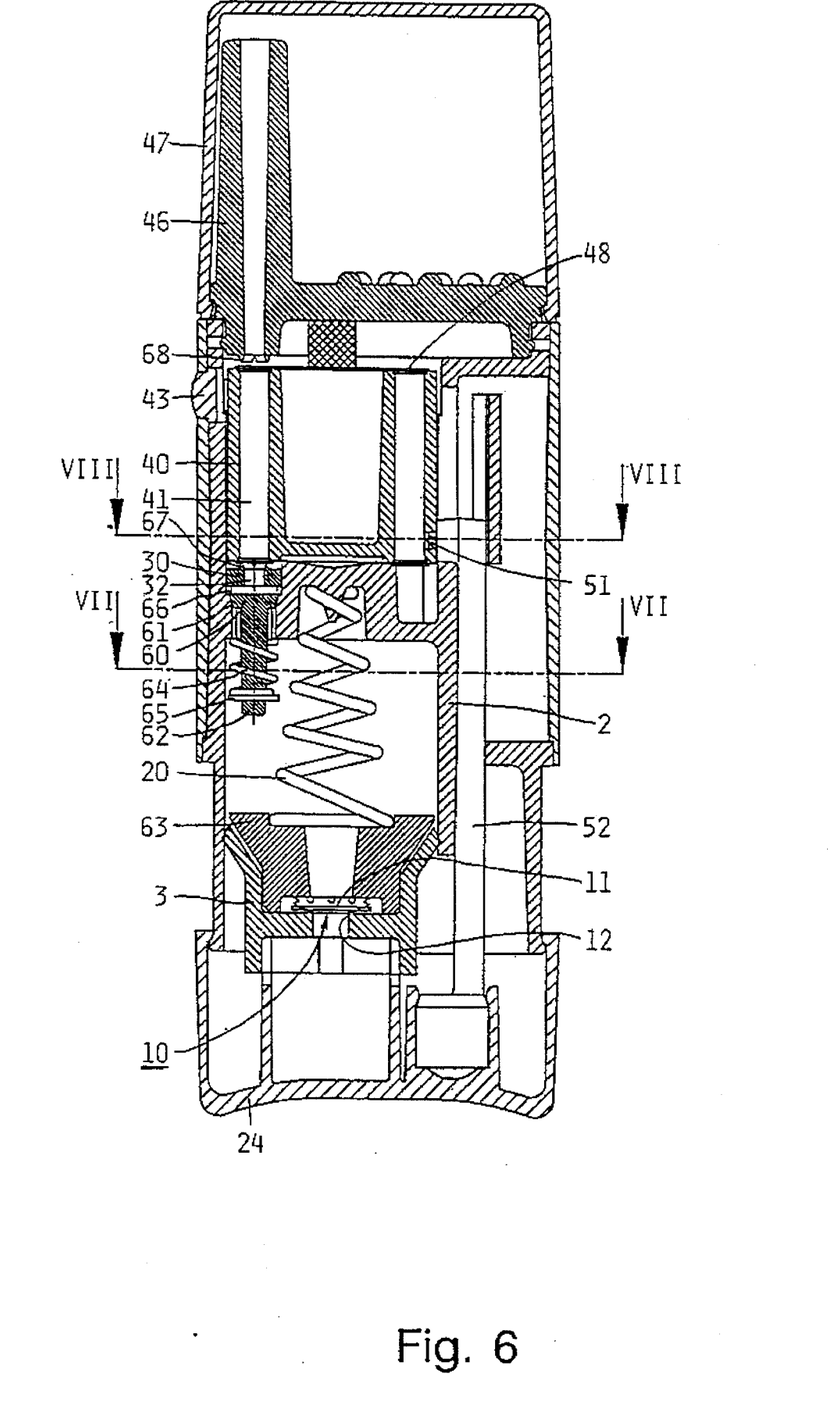
FIG. 6 shows a sectional side view of another embodiment of the device according to the invention.
Figure 7:
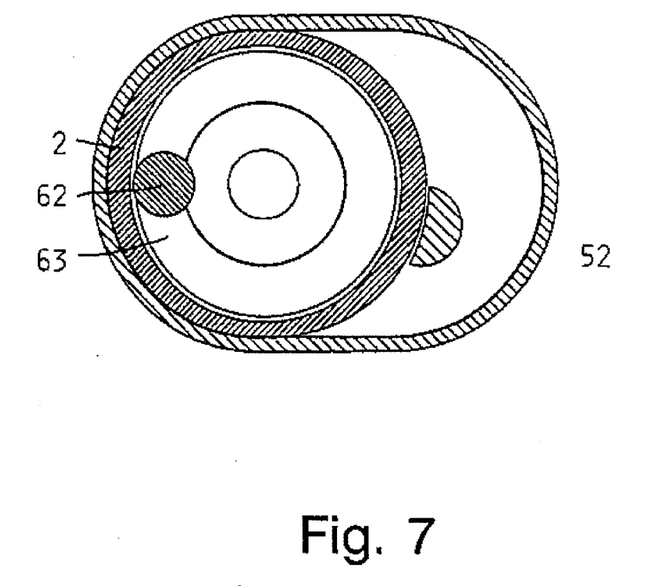
FIG. 7 shows a cross sectional view along the line VII—VII of the device shown in FIG. 6.
Figure 8:
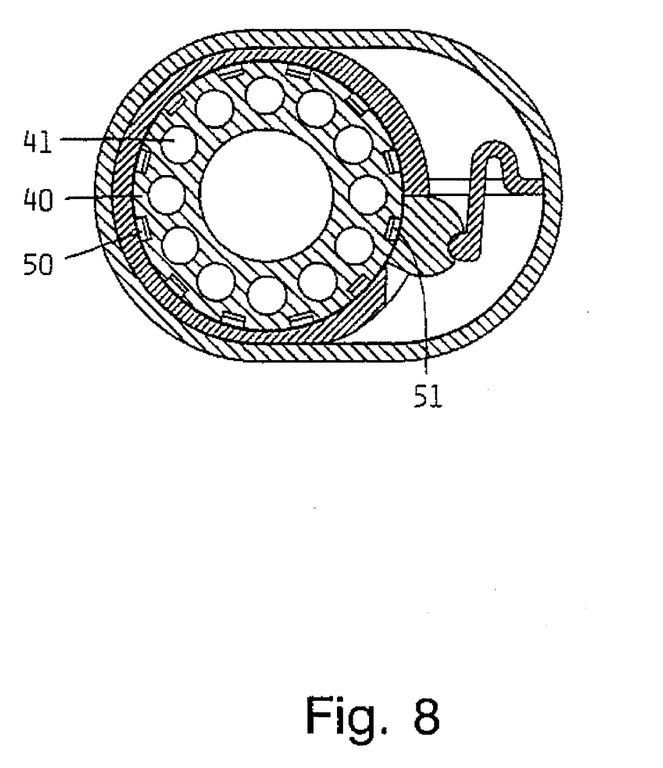
FIG. 8 shows a cross sectional view along the line VIII—VIII of the device shown in FIG. 6.

The embodiment shown in FIGS. 6–8 is similar to the embodiment shown in FIGS. 1–5, and corresponding details are specified by the same reference numbers.

The main difference between the two embodiments lies in the construction of the valve means bringing the interior of the cylinder in connection with the passage 32 through the penetrating means 30. In the embodiment according to FIG. 6 this valve means has the shape of a spring loaded valve having a valve head 60 closing against a valve seat 61 in the upper wall of the pressure cylinder 2, and having its stem 62 protruding through said upper wall into the interior of the cylinder. The air compressed in cylinder 2 is released through the gap formed between the valve head 60 and the valve seat 61. From the gap, the air may pass between the connections 66 to the upper side of the piston head 60 and further through the passage 32 through the penetrating means 30 to the inlet end of the chamber which is penetrated by this penetrating means. When the piston 3 is displaced to its innermost position a block 63 provided on the inner side of the piston will abut the end of the valve stem 62 and lift the valve head 60 from its seat 61 against the force of a helical spring 64 surrounding the valve stem and abutting at its one end the inner side of the upper wall of the cylinder and at its other end a washer 65 press fitted on the valve stem 62. The penetrating means 30 with its internal passage 32 has in this embodiment the shape of a short sleeve which is at one end connected to the valve head 60 by circumferencially spaced connections 66 so that the penetrating means is activated by the valve being lifted. The dispenser has a one-way valve 10 which is formed as a disk 11 sealing along a circumferential rib 12 surrounding an inlet hole when superatmospheric pressure is provided in the cylinder 2 by pressing the piston 3 inward.

The other end of the penetrating means 30 is almost the whole way round along the edge of its internal passage 32 provided with a sharp brim 67 fitting into the opening of the chamber 41 which is in the dispensing position. Hereby the membrane 48 of the chamber is cut free along the edge of the opening except for a thin rib which prevents the membrane piece cut free from being entrained by the air flow through the chamber. The membranes 48 are shown in FIG. 6.

After the membrane 48 at one end of the magazine has been cut by the penetrating means, this penetrator lifts the magazine pressing it against a corresponding sharp brim 68 provided at the inlet end of the dispensing pipe 46 to cut the membrane 48 at the other end of the magazine.

I claim:

1. A manually operated dispenser for dispensing a predetermined amount of a powdered substance, said dispenser comprising:

a) a pressure cylinder;
   b) a spring-loaded hollow piston axially displaceable in said cylinder;
   c) a one-way valve for intake of air into the cylinder;
   d) a passage having an inlet end and an outlet end;
   e) a dispensing pipe having an inlet end and an outlet end, the inlet end of the dispensing pipe being positioned opposite the outlet end of the passage;
   f) a magazine comprising a number of chambers extending through said magazine, each chamber containing a predetermined amount of powdered substance and having an inlet and an outlet covered by penetrable membranes;
   g) means for successively moving said magazine into a position in which one of said chambers is located with its inlet in proximity to the outlet end of said passage;
   h) a first penetrating means at the inlet end of the dispensing pipe for penetrating said membrane;
   i) a second penetrating means axially displaceable at the outlet end of the passage for penetrating said membrane;
   j) valve means connecting the interior of the cylinder to the inlet end of said passage; and
   k) means for displacing the second penetrating means axially towards the magazine and means for opening the valve means when the hollow piston is pressed to an inner position in the cylinder to provide a superatmospheric pressure in said cylinder.

2. A dispenser according to claim 1, wherein said valve means comprises a spring-loaded valve having a head and a stem, a valve seat in an upper wail of said cylinder, and a valve spring biasing said spring loaded valve closed with its head against the valve seat, said valve stem extending into said cylinder so far that it is engaged by the piston to open the spring loaded valve by lifting its head from the seat when the piston is pressed to its inner position in said cylinder.

3. A dispenser according to claim 1, wherein said valve means is carried on said hollow piston, said hollow piston and said cylinder both having a wall with a hole in said wall, the hole in the cylinder wall communicating with the inlet end of said passage and the hole in the piston wall communicating with the hole in the cylinder wall when the piston is pressed to its inner position in the cylinder.

4. A dispenser according to claim 3 or 2, wherein an elastic flap covers a hole in an end wall of said piston to provide the one-way valve.

5. A dispenser according to claim 1, 3 or 2 further comprising a housing which can be opened to mount the magazine inside it and which carries said dispensing pipe, the outlet end of said dispensing pipe designed for insertion into a nostril of a user.

6. A dispenser according to claim 1, 3 or 2, wherein the magazine is annular and comprises a number of tubular chambers which are spaced equidistantly from one another and from a longitudinal axis of the magazine, the chambers positioned parallel with the axis.

7. A dispenser according to claim 6 further comprising means for automatically rotating the annular magazine when a chamber has been emptied.

8. A dispenser according to claim 7, wherein the means for rotating the magazine comprises an activator by which the piston is pressed, a guide rod connected with this activator, a groove in an exterior cylindric surface of the annular magazine, this groove being composed of groove sections extending parallel with an axis of rotation of the magazine alternating with groove sections forming an angle with the axis of rotation, a free end of the guide rod engaging this groove.

9. A dispenser according to claim 2, wherein said second penetrating means is integral with said spring loaded valve and is displaced against the membrane closing the inlet of the chamber in the proximity to the outlet end of the passage when said spring-loaded valve is opened.

10. A dispenser according to claim 5, wherein the inlet end of the dispensing pipe is pointed.

11. A dispenser according to claim 5, wherein the housing comprises a lid having a hinge by which it is connected to a housing surrounding said pressure cylinder.

12. A dispenser according to claim 9, wherein a portion of said passage extends through the second penetrating means.

13. A dispenser according to claim 3, wherein said second penetrating means is mounted in a housing surrounding said cylinder and is axially displaceable in this housing, a pressure rod being mounted on an activator, said piston axially displaced when the piston is acted upon by the activator, the second penetrating means being positioned coaxially with the chamber at the outlet end of the passage, and displaced against the membrane covering the inlet of said chamber, when the activator is pressed.

14. A dispenser according to claim 13, wherein a portion of the passage extends through the second penetrating means.

* * * * *